United States Patent
Ulmsten et al.

(12) 
(10) Patent No.: US 7,112,210 B2
(45) Date of Patent: Sep. 26, 2006

(54) SURGICAL INSTRUMENT AND METHOD FOR TREATING FEMALE URINARY INCONTINENCE

(75) Inventors: Ulf Ulmsten, Danderyd (SE); Gene W. Kammerer, East Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 584 days.

(21) Appl. No.: 10/404,576

(22) Filed: Apr. 1, 2003

(65) Prior Publication Data

US 2003/0191480 A1  Oct. 9, 2003

Related U.S. Application Data

(63) Continuation of application No. 09/891,068, filed on Jun. 25, 2001, now abandoned.

(60) Provisional application No. 60/252,561, filed on Nov. 22, 2000.

(51) Int. Cl.
 *A61B 17/08* (2006.01)
 *A61F 2/00* (2006.01)
(52) U.S. Cl. .......................... 606/151; 600/29; 600/37
(58) Field of Classification Search ................ 606/151, 606/153, 154, 155, 157, 214; 600/29, 30; 128/898; 428/320.2, 321.5, 200, 40.1; 602/48, 602/54, 57, 58
See application file for complete search history.

(56) References Cited

U.S. PATENT DOCUMENTS

| | | | |
|---|---|---|---|
| 4,873,976 A | | 10/1989 | Schreiber |
| 5,259,835 A | * | 11/1993 | Clark et al. .................. 602/48 |
| 5,824,008 A | | 10/1998 | Bolduc et al. |
| 5,899,909 A | | 5/1999 | Claren et al. |
| 5,922,026 A | | 7/1999 | Chin |
| 5,934,283 A | | 8/1999 | Willem et al. |
| 6,042,534 A | | 3/2000 | Gellman et al. |
| 6,117,067 A | | 9/2000 | Gil-Vernet |
| 6,264,676 B1 | | 7/2001 | Gellman et al. |
| 6,273,852 B1 | | 8/2001 | Lehe et al. |
| 6,652,559 B1 | * | 11/2003 | Tetreault et al. ............ 606/214 |
| 6,872,227 B1 | * | 3/2005 | Sump et al. ................. 606/151 |

* cited by examiner

*Primary Examiner*—Julian W. Woo (57) ABSTRACT

The invention relates to a surgical instrument and a method for treating female urinary incontinence. A tape or mesh is permanently implanted into the body as a support for the urethra. In one embodiment, portions of the tape comprise tissue growth factors and adhesive bonding means for attaching portions of the tape to the pubic bone. In a further embodiment, portions of the tape comprise attachment means for fastening portions of the tape to fascia within the pelvic cavity. In both embodiments the tape is implanted with a single incision through the vaginal wall.

3 Claims, 13 Drawing Sheets

SURGICAL INSTRUMENT AND METHOD FOR TREATING FEMALE URINARY INCONTINENCE

CROSS REFERENCE TO RELATED APPLICATION

This application is a continuation of U.S. patent application Ser. No. 09/891,068 filed Jun. 25, 2001, now abandoned, and claims the benefit of earlier-filed U.S. provisional patent application, Ser. No. 60/252,561, filed on Nov. 22, 2000, which is incorporated herein by reference in its entirety.

FIELD OF THE INVENTION

The invention relates to a surgical instrument and a method for treating female urinary incontinence, i.e. the incapacity of controlling the discharge of urine.

BACKGROUND OF THE INVENTION

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

U.S. Pat. No. 5,899,909 discloses a surgical instrument comprising a shank having a handle at one end and connecting means at the other end to receive, one at a time, two curved needle-like elements which are connected at one end to one end of a tape intended to be implanted into the body. In practice, the tape is passed into the body via the vagina first at one end and then at the other end at one side and the other, respectively, of the urethra to form a loop around the urethra, located between the urethra and vaginal wall. The tape is extended over the pubis and through the abdominal wall and is tightened. The tape ends are cut at the abdominal wall, and the tape is left implanted in the body. U.S. Pat. No. 5,899,909 is hereby incorporated by reference in its entirety herein.

This invention simplifies the apparatus and method of the instrument and method prior art and provides for a safe and effective method of placing a tape mesh in a sling relationship with the urethra.

SUMMARY OF THE INVENTION

The object of the invention is to provide an improved and simplified surgery to restore urinary continence.

For this purpose the invention provides a surgical instrument for treating female urinary incontinence of the kind referred to above, comprising a tape or mesh (hereinafter collectively referred to as "tape") to be permanently implanted into the body as a support for the urethra. In one embodiment, portions of the tape comprise tissue growth factors and adhesive bonding means for attaching portions of the tape to the pubic bone. In a further embodiment, portions of the tape comprise attachment means for fastening portions of the tape to fascia within the pelvic cavity.

The invention also provides for a method for treating female urinary incontinence comprising the steps of creating an access way to the pelvic cavity via the vagina; passing a tape into the body via the access way first passing one end of the tape on one side of the urethra; passing the second end of the tape on the opposite side of the urethra to form a loop around the urethra, the tape located between urethra and the vaginal wall; and attaching the ends of the tape to the pubic bone or surrounding fascia. Preferably, in each embodiment the tape is left permanently in the body to provide, as an artificial ligament, the reinforcement of the tissue required in order to restore the urinary continence, and/or to provide said reinforcement by the development of fibrous tissue.

The object of the invention is to provide a surgical instrument and method for implanting a mesh to treat incontinence that does not require penetration of the abdomen.

An advantage of the invention is that it reduces the risk of perforating unintended body structures when carrying out the procedure.

These and other features and advantages of the present invention will become apparent from the following more detailed description, when taken in conjunction with the accompanying drawings which illustrate, by way of example, the principles of the invention.

DETAILED DESCRIPTION OF PREFERRED EMBODIMENTS

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

The invention discloses an apparatus and method for treating SUI. A tape is passed through pelvic tissue and positioned underneath the urethra, creating a supportive sling. The tape provides a structure means for tissue ingrowth and thereby provides a newly created body tissue supporting means for the urethra. When pressure is exerted upon the lower abdomen, such as during a cough or sneeze, the tape provides support to the urethra, allowing it to keep its seal and prevent the unwanted discharge of urine.

Referring to FIGS. 1a–c and 2, tape 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., a Johnson & Johnson company located at Somerville, N.J., U.S.A. This material is approved by the U.S. Food and Drug Administration for implantation into the human body. A still further embodiment of the tape 12 is a combination of a synthetic material 11 and a natural material 13 centered between the synthetic material 11. A still further embodiment of the tape 12 includes a combination of synthetic material 11 and natural material 13, whereby the natural material is placed over or incorporated within a generally central portion of the synthetic material 11. One advantage of the tape configurations is that natural material 13 is along the center region of tape 12 so that after installation of tape 12, natural material 13 is positioned below the urethra and eliminates possible erosion issues at the interface of the urethra and tape. Natural material 13 may be connected to the synthetic material 11 by means of sewing, a bio-compatible glue, cell culturing techniques or other known means.

Tape 12 may be of any convenient shape that suits the intended purpose of the invention. An exemplary width is about 1 cm and the length would be dependent upon the size of the female undergoing the procedure. Tape 12 may be single or double ply, generally planar in structure, or tubular to provide additional supporting strength and more surface area on which tissue fibers may attach. Moreover, tape 12 may consist of different types of material, such as a bioabsorbable and non-bioabsorbable material. Tape 12 may also be coated with an antimicrobial additive to prevent or minimize infection and a lubricous coating, for example, a bioabsorbable hydrogel, to facilitate the tape passing through the tissue as discussed below.

In one embodiment the tape comprises growth factors for stimulating cell growth at the interface of the tape and pubic bone. Growth factors may include natural or recombinant proteins (TGF-$\beta_1$, TGF-$\beta_2$, TGF-$\beta_3$, BMP-2, BMP-4, BMP-7, pleiotrophin, bone sialoprotein, osteopontin, endothelin, PTH, sonic hedgehog), mixtures (autologous growth factors, Emdogain, demineralized bone matrix, BMP extracts), transcription factors (cbfa-1), small molecures (PGE$_1$, PGE$_2$, peptide analogs of growth factors, P15, PTH, PTH 1–34, Chrysalin) or plasmids containing genes for any of the above molecules. Bone formation at the interface of the pubic bone and tape may also be induced by adding bone marrow cells, mesenchymal stem cells, osteoblasts or microvascular tissues or engineered cell lines or primary cells.

There are many methods of attaching the growth factors to the tape, which must be chosen with a specific growth factor in mind, as is well known to those skilled in the art. Attachment methods include: covalent attachment with or without a linker or spacer molecule; attachment via an affinity ligand; physical adsorption to the tape; encapsulation on the surface via ploymers, liposomes or gels; lyophilization onto the mesh (with co-precipitates such as mannose or albumin); or wetting the tape at the time of surgery with a solution, gel or slurry containing the growth factor.

Figure 1A:
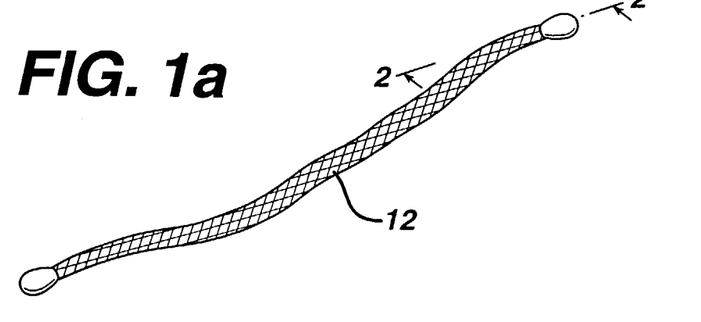
FIGS. 1a–c are alternate embodiments of the tape.
Figure 1B:
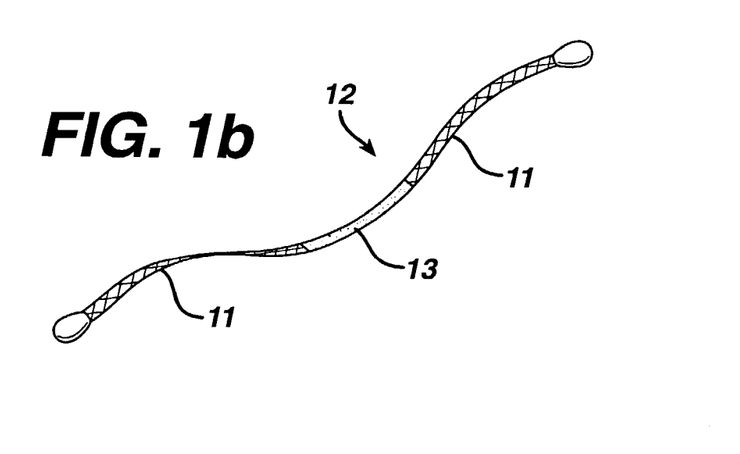
Figure 1C:
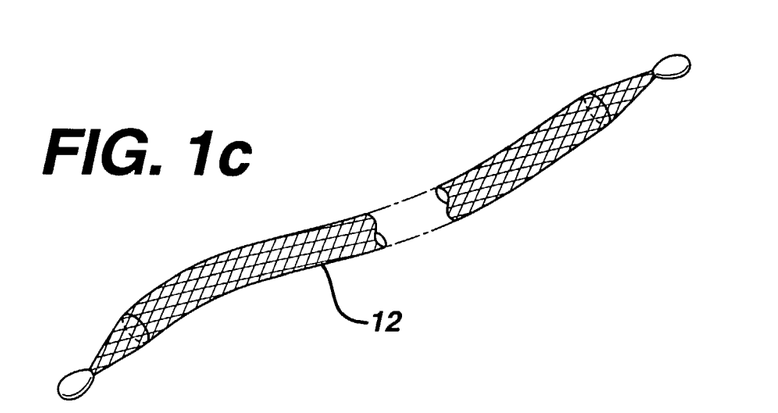
Figure 2:
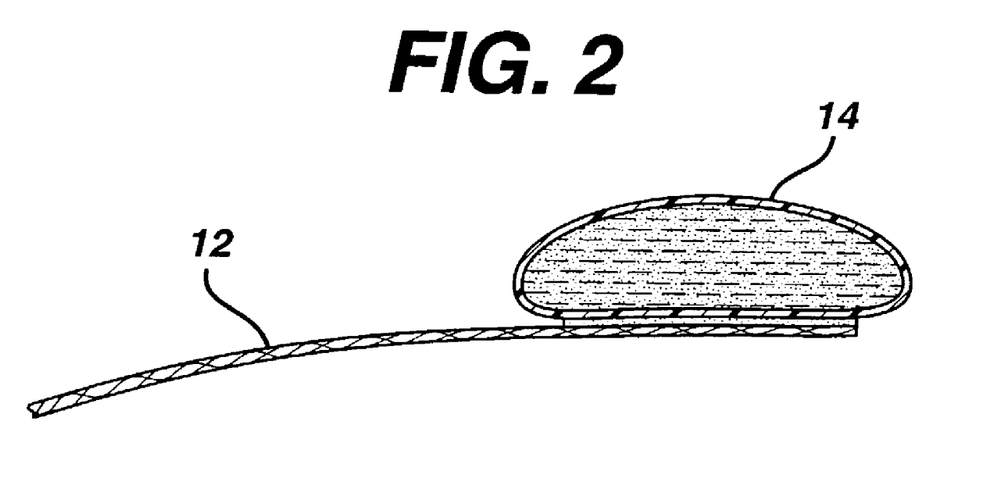
FIG. 2 is a cut-away elevation view of the tape of FIG. 1.

Referring to FIG. 2, the ends of the tape 12 may be modified to include an easily breakable pouch 14, 16 (not shown) containing an adhesive for bonding the tape to the pubic bone. This allows the surgeon to manipulate the tape within the body and once in place, burst the pouch to free the adhesive and bond the tape to the pubic bone as described in more detail below. Examples of bonding adhesives include fibrin glues; di isocyanates; glutaraldehyde; cyano acrylates; thiolactones; carbodiimides; mussel adhesive protein; poly amino acid adhesives; photo crosslinked acrylates; PMMA (bone cement); and bis-GMA (dental cement).

The surgical procedure for implanting tape 12 is shown in FIGS. 3a–e utilizing the tape embodiment of FIG. 2. In the figures the relevant parts of the female lower abdomen are disclosed, the vagina being 50, the uterus 52, the urethra 54, the pubic bone 56, the urinary bladder 58 and the abdominal wall 60.

The surgeon first prepares an incision in the vaginal wall, creating a tissue flap. The surgeon performs a blunt dissection of the tissue on one side of the urethra to create a channel from the vaginal incision to the pubic bone. At this point the surgeon is able to guide a finger from the vaginal incision, around the urethra and to the backside of the pubic bone. Preliminary measurements may be made to determine the length of tape required for the procedure. Preferably, multiple lengths of tape are available, each with adhesive pouches 14, 16 at both ends of the tape. For an average-sized female, tape 12 is about 10 cm long. The surgeon passes the first end of tape 12 through the incision and positions the tape end at approximately the mid-line at the back side of the pubic bone 56 and attaches the tape to the pubic bone by bursting the adhesive-containing pouch 14, simply by pressing the pouch against the pubic bone, FIGS. 3a–c.

Figure 3A:
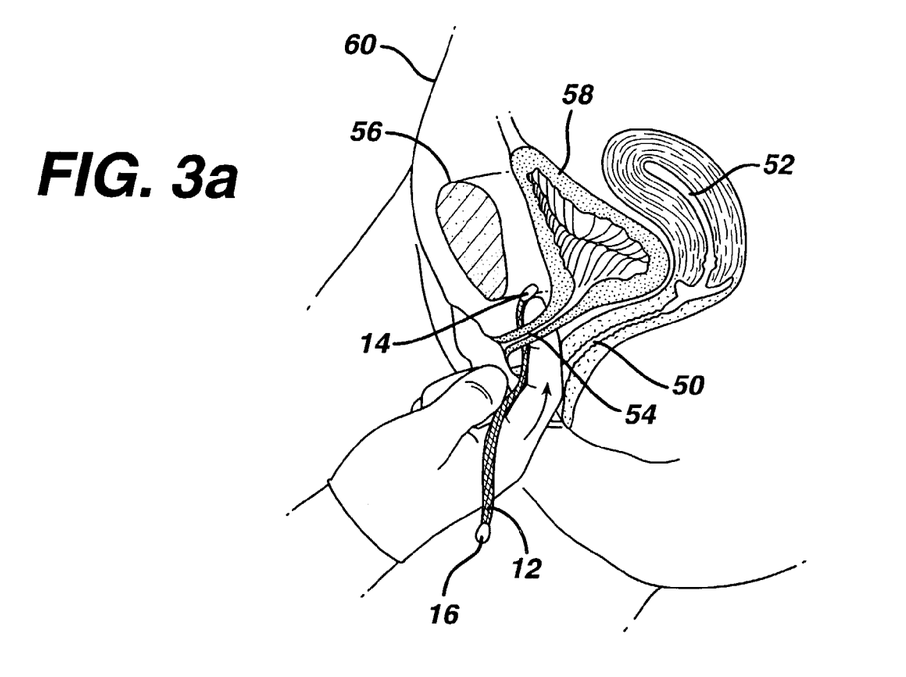
FIGS. 3a–f illustrate diagrammatically one embodiment of several surgical steps of the method for inserting a tape according to the invention
Figure 3B:
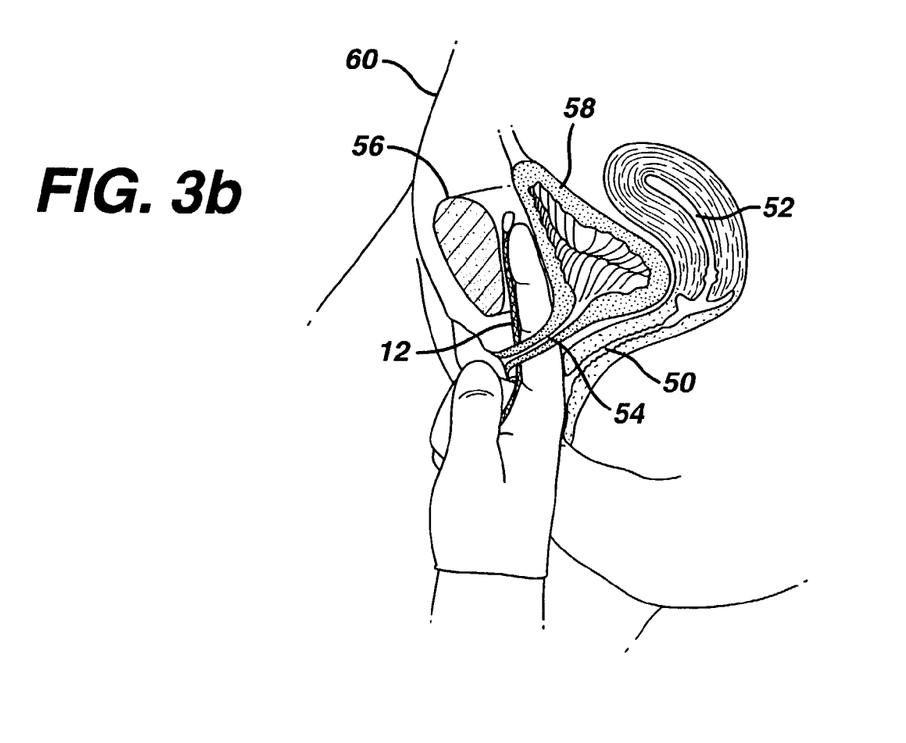
Figure 3C:
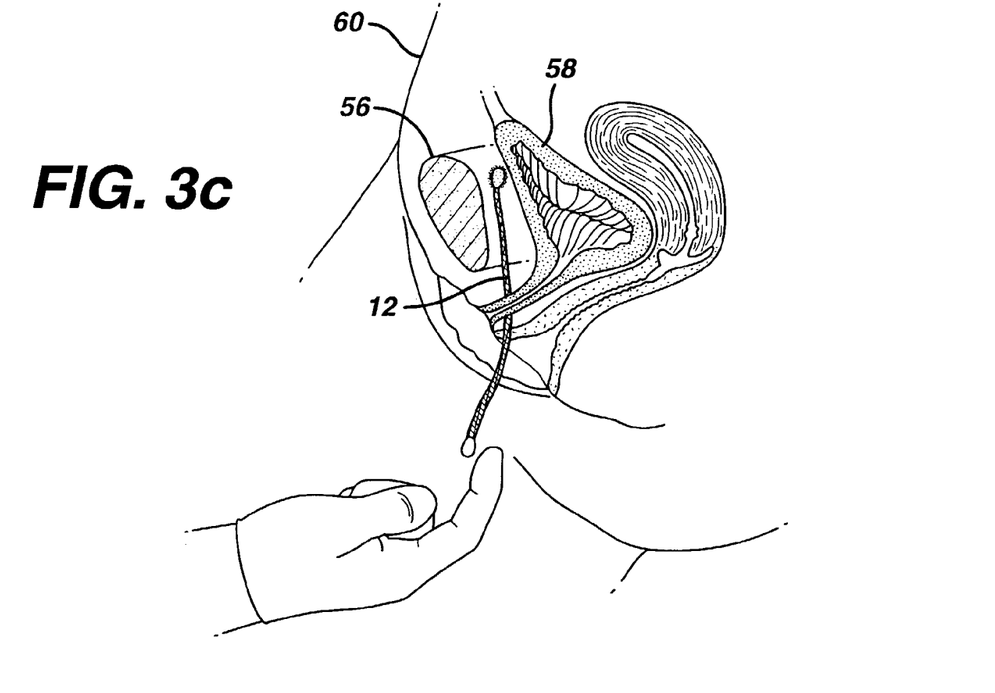
Figure 3D:
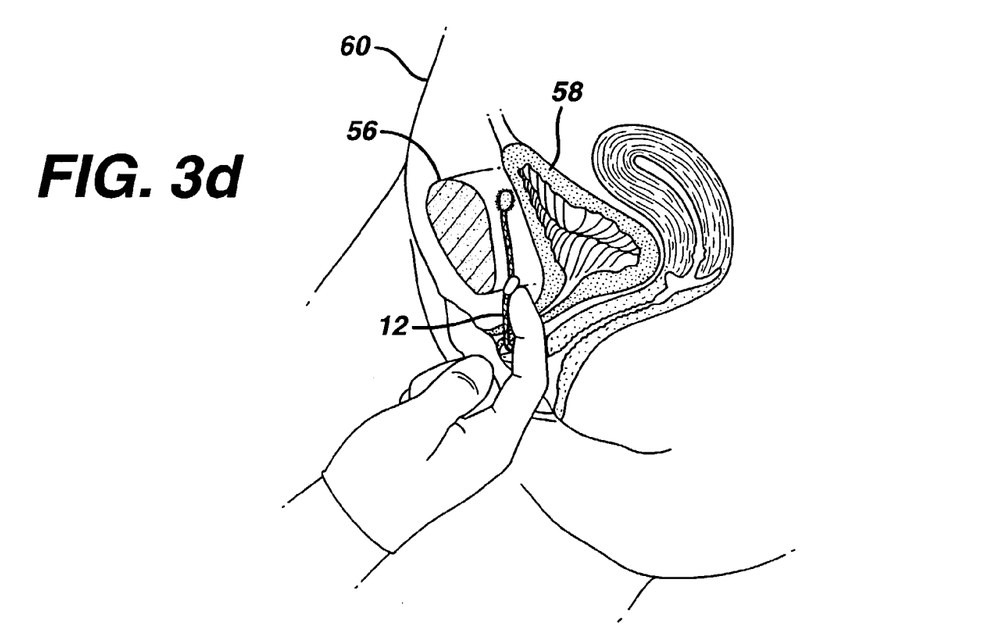
Figure 3E:
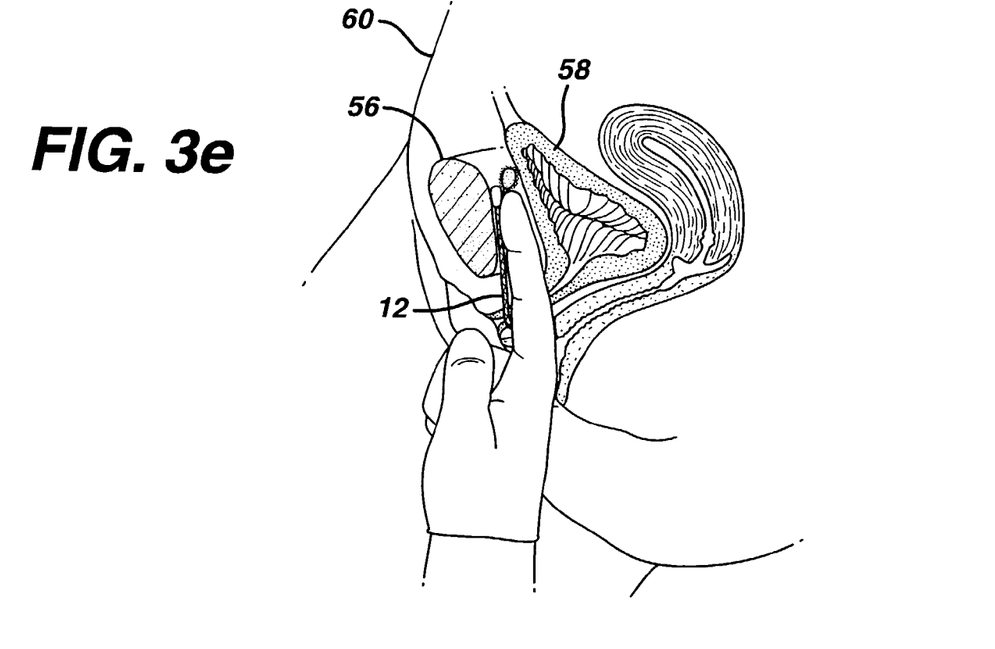
Figure 3F:
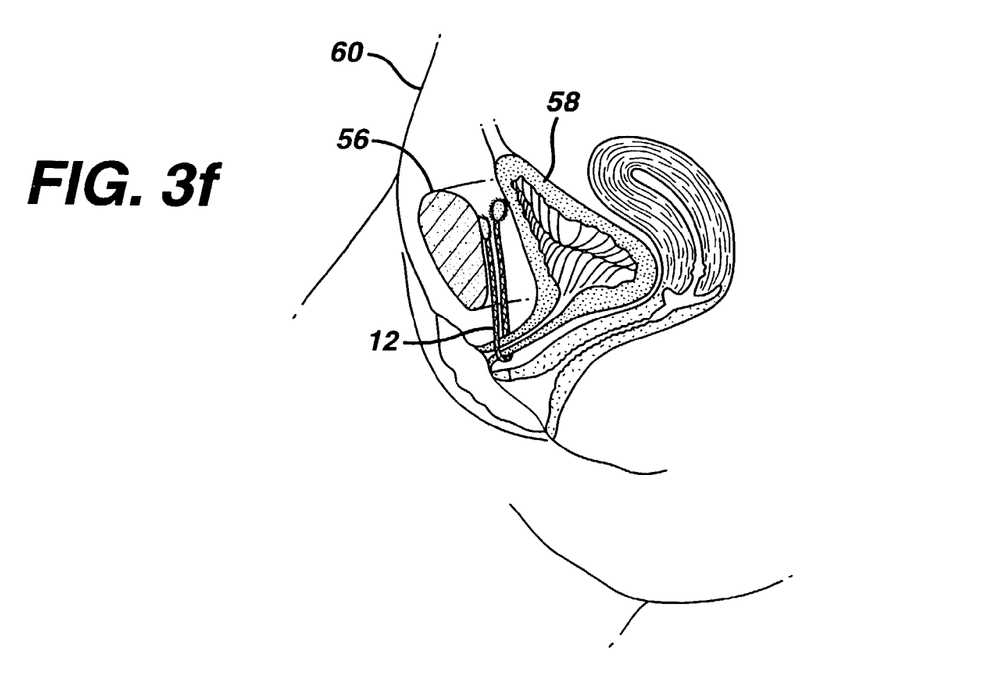

The surgeon then performs a blunt dissection of the tissue on the opposite side of the urethra and passes the second end of tape 12 through the incision in the vaginal wall and through the soft tissue, on the opposite side of the urethra than the previous end of tape 12. The surgeon may hold the tape in place while a urodynamic test is performed to check the integrity of the urethra to ensure the proper position of the tape. The position of the second end of tape 12 at the pubic bone may be adjusted according to the results of the urodynamic test. Once the proper position of the second end of tape 12 is established in relation to the pubic bone, the surgeon again bursts pouch 16 thereby releasing the bone adhesive, FIGS. 3d–f. Tape 12 may further comprise means for post-operative adjustment as is described in pending U.S. patent application, Ser. No. 09/589,242 filed on Jun. 7, 2000, entitled Method and Apparatus for Adjusting Flexible Areal Polymer Implants, which is hereby incorporated herein by reference in its entirety.

Table 1, below, provides the average attachment force of BIOGLUE and DERMABOND when used to attached a PROLENE mesh tape to the pelvic bone in an animal study.

TABLE 1

AVERAGE ATTACHMENT FORCE (lbs.)

| Time Period | BioGlue | DERMABOND |
|---|---|---|
| 0 day | 1.36 | 2.83 |
| 2 week | 2.04 | 1.93 |
| 3 week | 2.40 | 9.2 |
| 4 week | 2.32 | 2.49 |
| 6 week | 2.76 | 3.11 |

Figure 5:
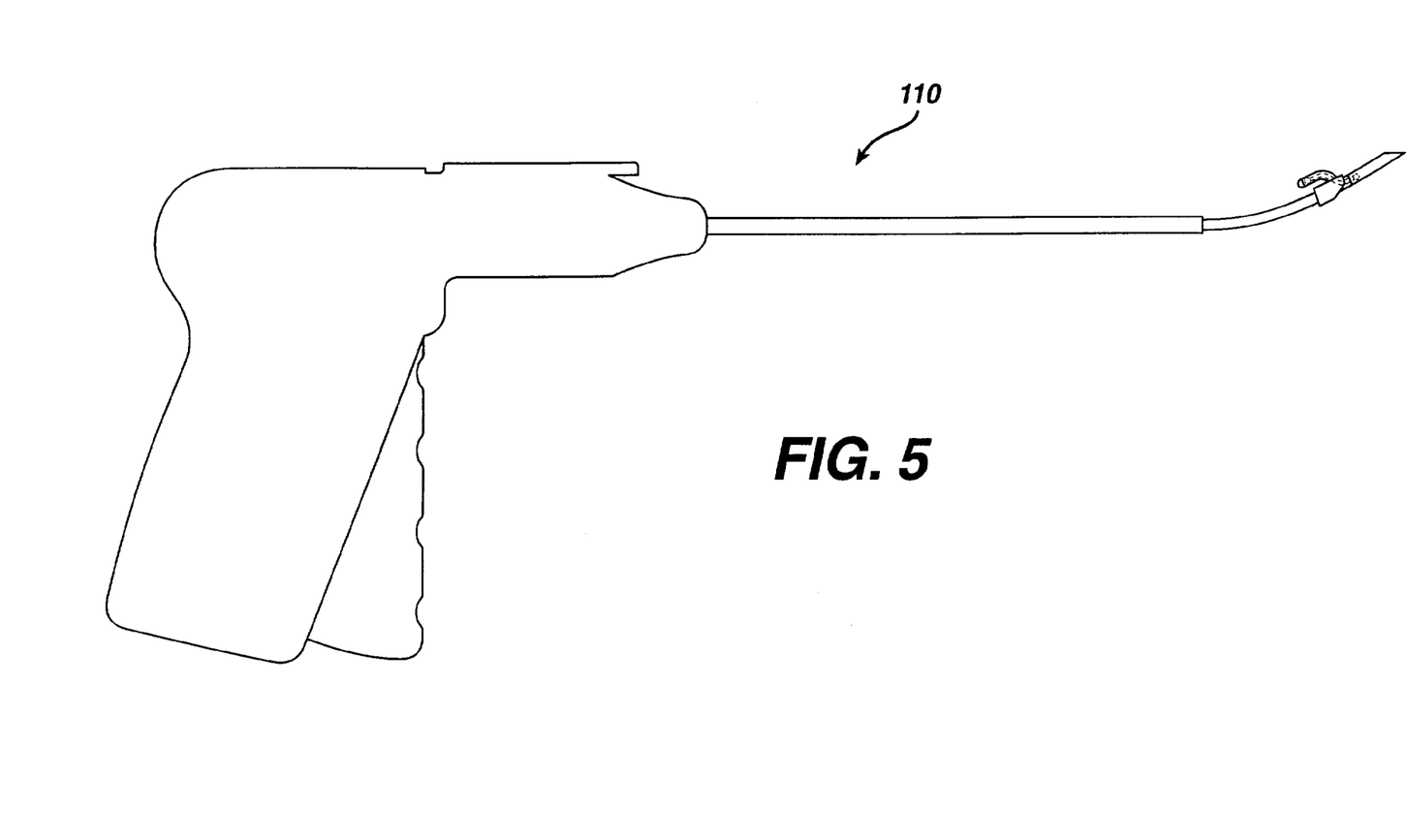
FIG. 5 illustrates an apparatus for fastening the tape into fascia in the lower abdomen.
Figure 6A:
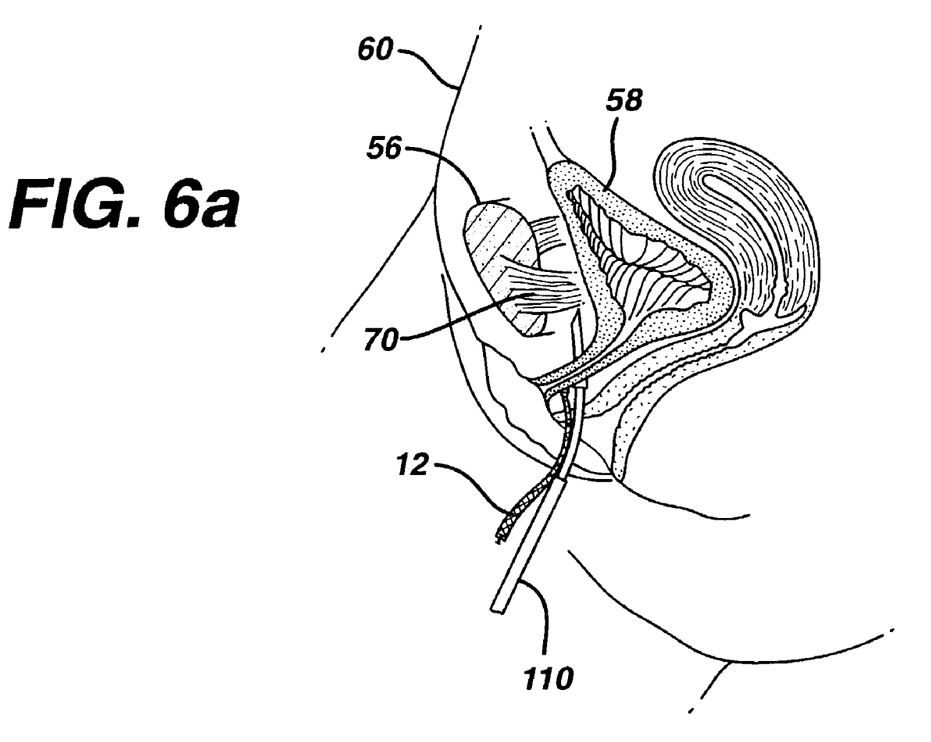
FIGS. 6a–e illustrate diagrammatically an alternate embodiment of several surgical steps of the method for inserting a tape according to the invention.
Figure 6B:
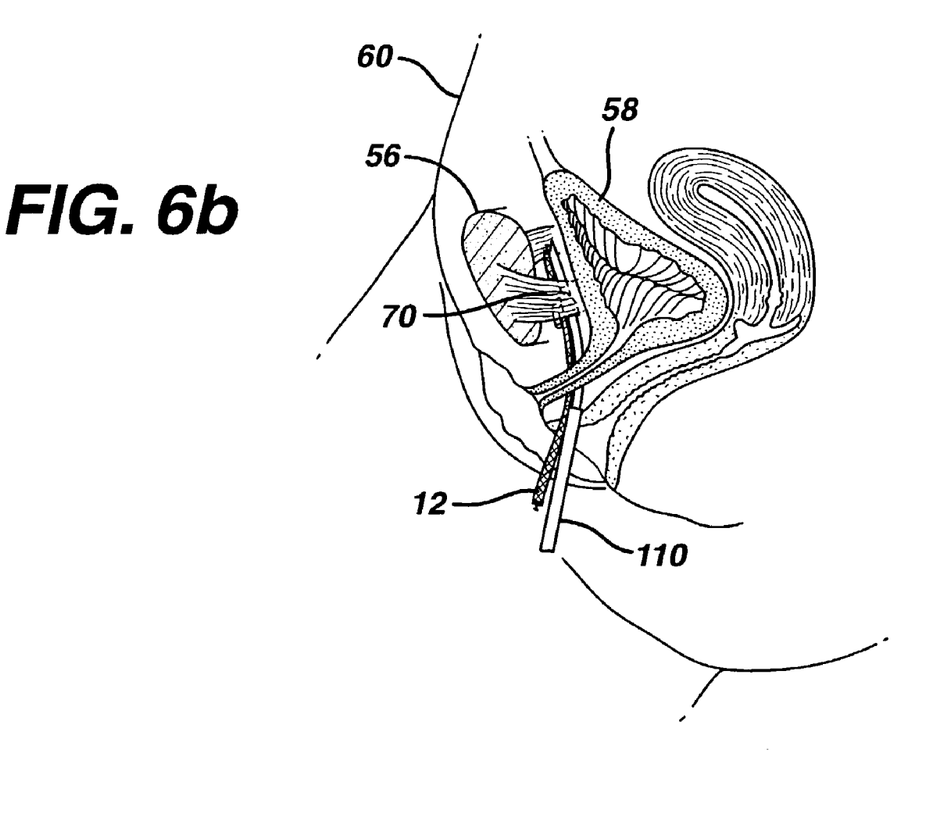
Figure 6C:
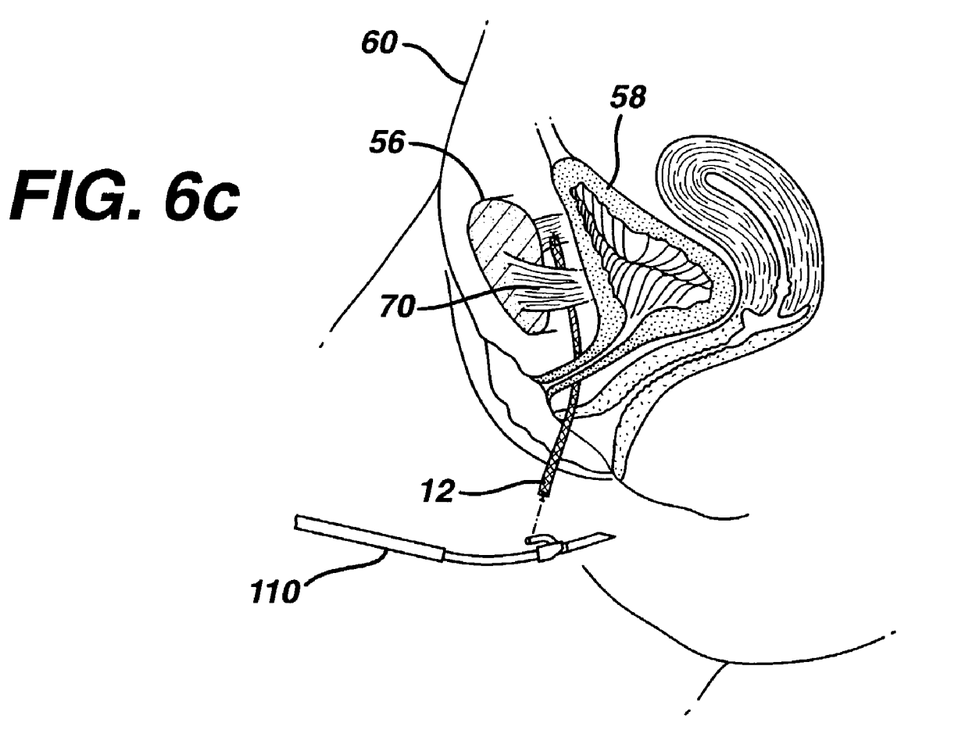
Figure 6D:
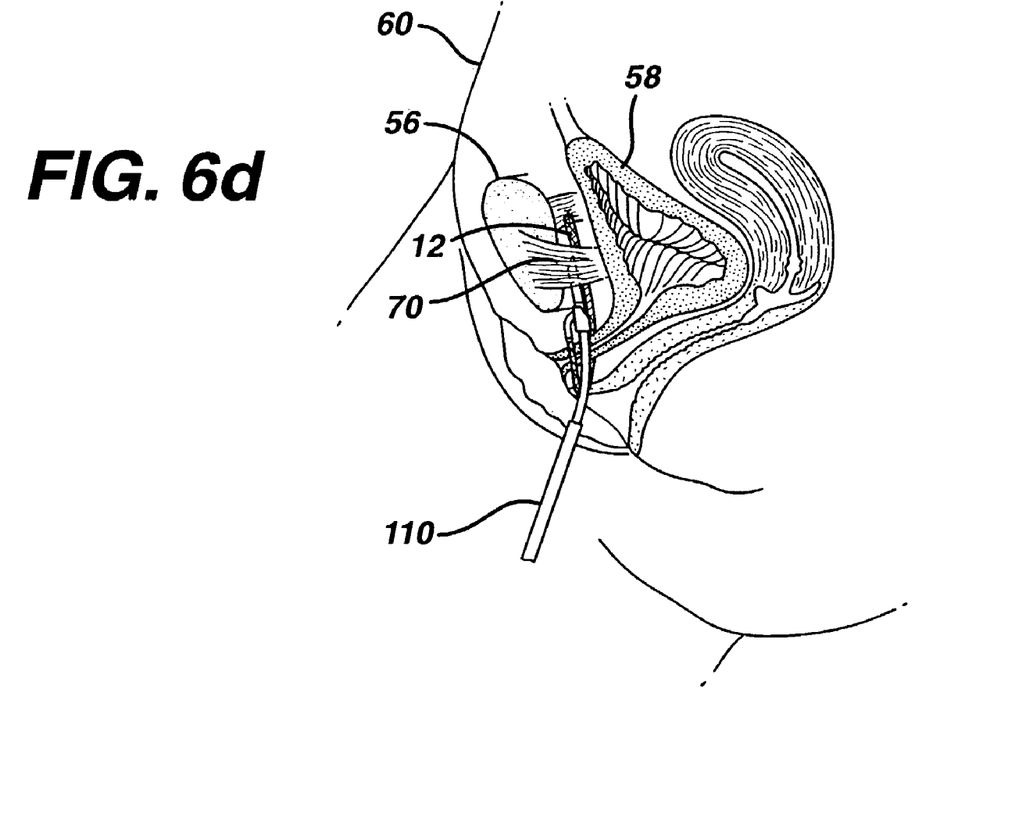
Figure 6E:
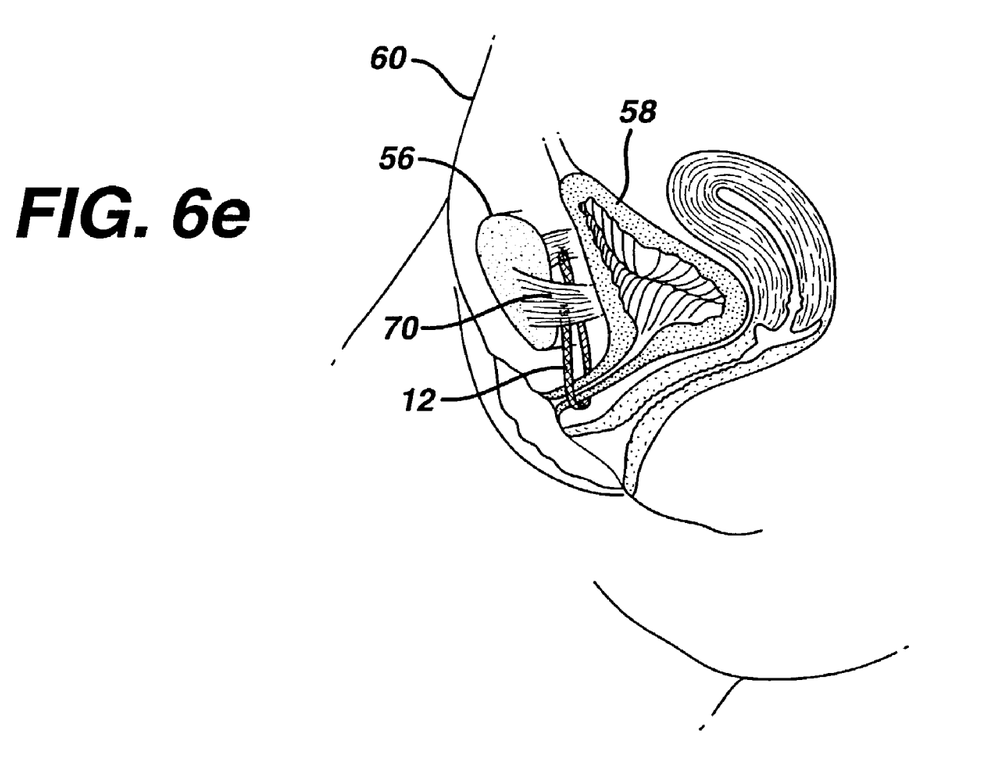

In an alternate embodiment, the ends of tape 12 are secured within fascia surrounding the pubic bone 56 using an applicator 110 (FIG. 5). This embodiment takes advantage of the Mitek Meniscal Repair System, as disclosed in U.S. Pat. No. 5,941,439, and sold by Mitek, a business unit of Ethicon, Inc., a Johnson & Johnson company. A preferred applicator is product code 228000 with a 34° needle, product code 228218.

Figure 4:
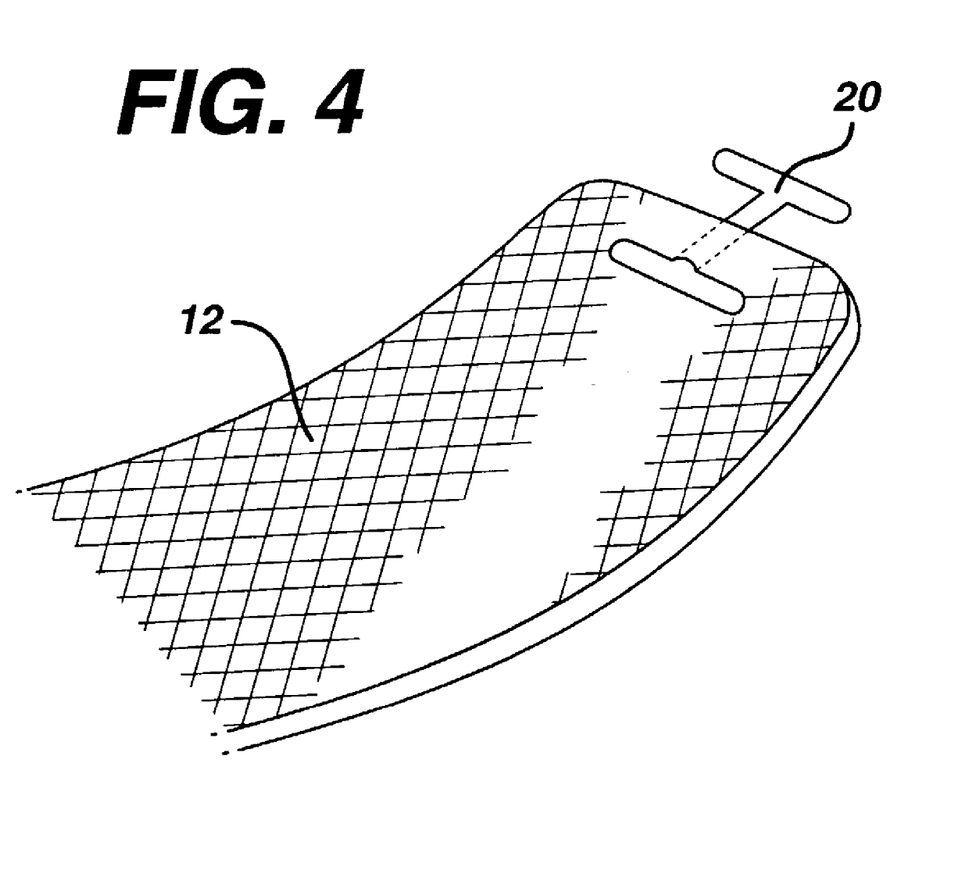
FIG. 4 illustrates a fastener in combination with a tape for use in inserting the tape in accordance with an alternate embodiment of the invention.

As shown in FIG. 4, an "H" fastener 20, 10 mm long with 4 mm legs, is attached to both ends of a tape 12. The fastener may be made biodegradeable material, such as PDS suture material or a non-biodegradeable material, such as polypropolene. One leg passes completely through one end of the tape 12, and the other leg loads into the Mitek applicator, as shown in FIG. 5.

The surgical procedure for implanting tape 12 is shown in FIGS. 6a–e utilizing the tape embodiment of FIG. 4. Using the same preparatory procedures stated above, the sugeon guides the applicator through the dissected area on the right side of the urethra, FIG. 6a. The needle and tape are brought in contact with the cooper's ligament 70 at the inferior lateral aspect of the pubic bone, FIG. 6b. The fastener is deployed into the tissue where the legs are released into and captured by the tissue, FIG. 6c. The mesh is placed beneath the urethra and the second end of the tape is attached to similar tissue on the left side of the urethra, FIGS. 6d–e. Adjustments to the length of the tape may be made by simply placing the fastener at shorter or longer lengths along the tape. Further, adjustments to the length may be made after initial deployment by deploying a third fastener through the mesh and into the tissue at some shorter tape length. Again, post-operative adjustments may be accomplished via the means disclosed in U.S. patent application, Ser. No. 09/589,242.

Although the preferred embodiment for the fastener is an H-shaped device, other configurations can be utilized. Exemplary shapes may include a hooked-shaped device, arrow-shaped fasteners, and T-shaped fasteners. Further, the fastener may be a large mass, such as a knot, which is held within the tissue. Still further, more than one fastener may be attached to each end of tape 12 to increase the amount of tissue captured by each fastener.

Figure 7:
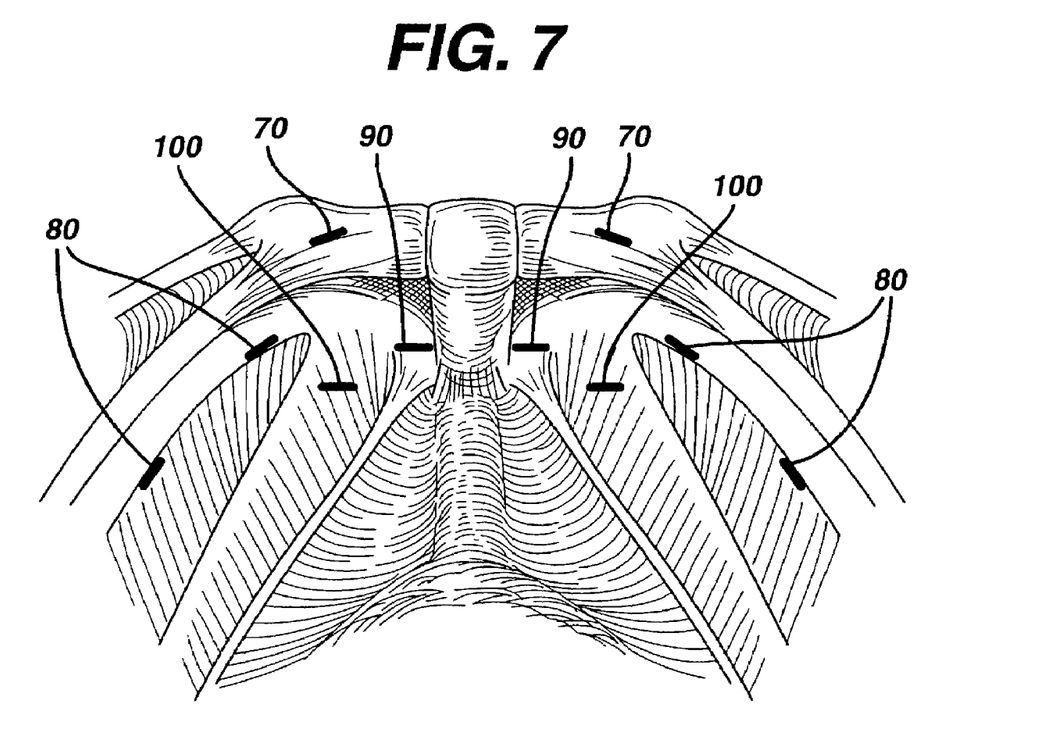
FIG. 7 illustrates exemplary tissues within the lower abdomen to which the tape is fastened.

As would be appreciated by those skilled in the art, there exist multiple tissue areas within the pelvic area in which to attach the mesh. Referring to FIG. 7, examples include the obturator foramen 80, the pubourethral ligaments 90 and the levator ani muscle 100.

In still a further embodiment, a guide system or cannula may be employed to guide the applicator through the tissue so that less blunt dissection is required. The cannula may be pre-dimensioned and act as a template to effectively position the application. Preferably, the cannula has graduations or dimension marks so the surgeon is able to accurately determine the depth of penetration of the cannula and applicator.

A still further embodiment includes a combination of the two previous methods and apparatus. For example, the surgeon may attach the first end of the tape to the pubic bone using an adhesive as previously described and attaching the second end of the tape to tissue. One advantage of this technique is that the second attachment using a fastener allows for adjustment if the tape is too loose as previously discussed.

An additional embodiment includes combining the growth factors and the fastener on both ends of the tape. The fasteners work as the primary attachment modes and the growth factors work as the final attachment modes. In this case fast absorbing materials, such as collegen or regenerated cellulose can be use as the fasteners. The advantage being that the solid fasteners do not remain in the uro/genital area for any significant length of time.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A device for treating female urinary incontinence in a patient, comprising:
    a substantially flat, flexible tape for providing a sling under the urethra, and having first and second ends;
    first and second pouches at first and second ends of the tape respectively;
    an adhesive contained within the first and second pouches;
    wherein the first and second pouches are configured to release the contained adhesive when a predetermined amount of pressure is applied to the pouches, and wherein the tape is comprised of a combination of bioabsorbable and non-bioabsorbable materials.

2. The device according to claim 1, wherein the tape further comprises growth factors for stimulating cell growth.

3. The device according to claim 2, wherein the tape comprises growth factors at least in the areas in which the tape interfaces with the bone when implanted in the patient.

* * * * *